United States Patent
Alanine et al.

[19]

[11] Patent Number: 6,015,824
[45] Date of Patent: Jan. 18, 2000

[54] PYRROLIDINE AND PIPERIDINE DERIVATIVES AND TREATMENT OF NEURODEGENERATIVE DISORDERS

[75] Inventors: Alexander Alanine, Riedisheim, France; Bernd Büttelmann, Schopfheim, Germany; Marie-Paule Heitz Neidhart, Hagenthal le Bas; Emmanuel Pinard, Linsdorf, both of France; René Wyler, Zürich, Switzerland

[73] Assignee: Hoffmann-La Roche AG, Nutley, N.J.

[21] Appl. No.: 09/234,266

[22] Filed: Jan. 20, 1999

[30] Foreign Application Priority Data

Feb. 10, 1998 [EP] European Pat. Off. ............. 98102246

[51] Int. Cl.[7] ........................ A61K 31/42; A61K 31/445; A61K 31/535; C07D 263/52; C07D 471/04
[52] U.S. Cl. ................. 514/375; 514/230.5; 514/302; 544/105; 546/115; 546/116; 548/217
[58] Field of Search ............................. 548/217; 514/375, 514/302, 230.5; 546/115, 116; 544/105

[56] References Cited

U.S. PATENT DOCUMENTS

| | | | |
|---|---|---|---|
| 3,941,796 | 3/1976 | Sankey et al. | 260/293.84 |
| 4,407,670 | 10/1983 | Crabb | 71/67 |
| 4,548,951 | 10/1985 | Muchowski et al. | 514/522 |
| 4,558,066 | 12/1985 | Waterbury | 514/422 |

FOREIGN PATENT DOCUMENTS

| | | |
|---|---|---|
| 050 370 | 10/1981 | European Pat. Off. . |
| 071 399 | 7/1982 | European Pat. Off. . |
| 114 758 | 1/1984 | European Pat. Off. . |
| 115 413 | 1/1984 | European Pat. Off. . |

OTHER PUBLICATIONS

G. Fischer, V. Mutel, G. Trube, P. Malherbe, J.N.C. Kew, E. Mohacsi, M.P. Heitz and J. A. Kemp, J. of Pharmacology & Expermental Therapeutics, 283, (1997), 1285–1292.
H.–P. Kaiser and J. M. Muchowski, J. Org. Chem., 49, (1984), 4203–4209.

*Primary Examiner*—Evelyn Mei Huang
*Attorney, Agent, or Firm*—George W. Johnston; Dennis P. Tramaloni; Joseph P. Kirk, Jr.

[57] ABSTRACT

The present invention relates to the use of pyrrolidine and piperidine derivatives of the general formula

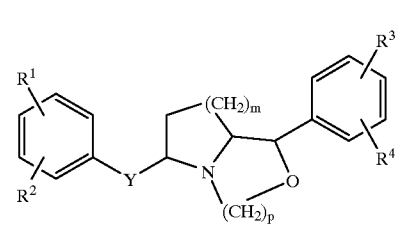

II wherein
$R^1$ and $R^2$ are, independently from each other, hydrogen, lower alkoxy, hydroxy, halogen, —$CONH_2$ or —C(O)O-lower alkyl; or taken together are —O—$CH_2$O;
$R^3$ and $R^4$ are, independently from each other, hydrogen, lower alkoxy, benzyloxy, halogen, hydroxy, —$CONH_2$ or —$SCH_3$; or taken together are —O—$CH_2$—O—;
Y is —CH(OH)—, —$(CH_2)_n$—, —C(O)— or —CH (lower alkoxy)—; and
m, n and p are 1 or 2;
and to their pharmaceutically acceptable addition salts for the treatment of diseases caused by over activation of NMDA receptor subtypes.

5 Claims, No Drawings

PYRROLIDINE AND PIPERIDINE DERIVATIVES AND TREATMENT OF NEURODEGENERATIVE DISORDERS

INTRODUCTION

The present invention relates to the use of pyrrolidine and piperidine derivatives of the general formula I and II:

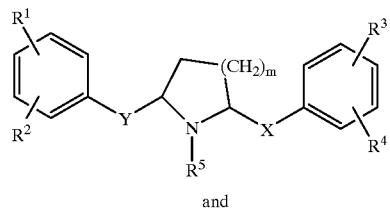

I and

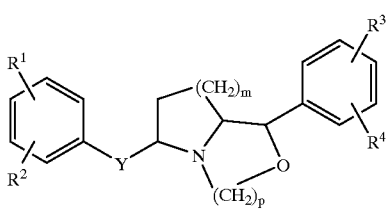

II wherein $R^1$ and $R^2$ are, independently from each other, hydrogen, lower alkoxy, hydroxy, halogen, —$CONH_2$ or —C(O)O—lower alkyl; or taken together are —O—$CH_2$;

$R^3$ and $R^4$ are, independently from each other, hydrogen, lower alkoxy, benzyloxy, halogen, hydroxy, —$CONH_2$ or —$SCH_3$; or taken together are —O—$CH_2$—O—;

$R^5$ is hydrogen or lower alkyl;

X and Y are, independently from each other —CH(OH)—, —$(CH_2)_n$—, —C(O)— or —CH (lower alkoxy)—; and m, n and p are 1 or 2;

and to their pharmaceutically acceptable addition salts for the treatment of diseases caused by over activation of NMDA receptor subtypes.

SUMMARY OF THE INVENTION

Objects of the present invention are the use of compounds of formula I and II in the treatment or prophylaxis of diseases caused by over activation of respective NMDA receptor subtypes, which include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and, diseases such as schizophrenia, anxiety and depression, the use of these compounds for manufacture of corresponding medicaments, and novel compounds of formula II

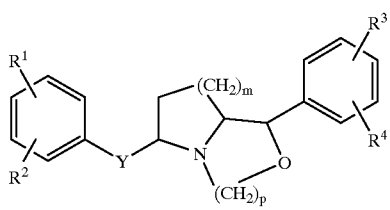

II wherein $R^1$ and $R^2$ are, independently from each other, hydrogen, lower alkoxy, hydroxy, halogen, —$CONH_2$ or —C(O)O-lower alkyl; or taken together are —O—$CH_2$—O—;

$R^3$ and $R^4$ are, independently from each other, hydrogen, lower alkoxy, benzyloxy, halogen, hydroxy, —$CONH_2$ or —$SCH_3$; or taken together are —O—$CH_2$—O—;

Y is —CH(OH)—, —$(CH_2)_n$—, —C(O)— or —CH (lower alkoxy)—; and m and p are 1 or 2.

Additional objects of the present invention include processes for the manufacture of these novel compounds, medicaments, containing them, the use of these compounds in the above mentioned kind and for the manufacture of corresponding medicaments.

DETAILED DESCRIPTION

Compounds of formula I and their salts are known compounds. They are described to possess activities for the treatment of the following diseases:

ophthalmic diseases caused by increased intraocular pressure, such as glaucoma (U.S. Pat. No. 4,558,066), cardiovascular diseases (EP 114 758, U.S. Pat. No. 4,548,951 and EP 115 413), hypertension, cardiac arrhythmia and vasal congestion (EP 71 399), hypertension, cardiac arrhythmia and allergic diseases (EP 50 370), and bronchodilator activity (U.S. Pat. No. 3,941,796), while the compounds of formula II are new and novel.

Despite the understanding by those skilled in the art of the above identified activities of the compounds of formula I and II of the present invention, the activities described herein and subject of this invention have previously been neither recognized nor understood. It has now surprisingly been found that compounds of the present invention are NMDA (N-methyl-D-aspartate)-receptor-subtype selective blockers, which have a key function in modulating neuronal activity and plasticity which makes them key players in mediating processes underlying development of CNS including learning and memory formation and function.

Under pathological conditions of acute and chronic forms of neurodegeneration, over activation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in N1NMDA receptors, displaying different pharmacological properties. Possible therapeutic indications for NMDA receptor subtype specific blockers include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and, diseases such as schizophrenia, anxiety and depression.

As used herein the following definitions of the general terms used in the present description apply irrespective of whether the terms in question appear alone or in combination.

The term "lower alkyl" denotes a straight or branched-chain alkyl group containing from 1 to 4 carbon atoms, for example, methyl, ethyl, propyl, isopropyl, n-butyl, i-butyl, 2-butyl and t-butyl.

The term "halogen" denotes chlorine, iodine, fluorine and bromine.

The term "lower alkoxy" denotes a group wherein the alkyl residue is as defined above.

The compounds of the invention can be prepared in possible stereoisomeric forms, and may exist as stereochemically pure forms: as racemic mixtures containing both members of one enantiomeric pair from the total of four such pairs; or as mixture of some of all of the diastereomeric forms. The invention is intended to encompass all of these possibilities.

Preferred compounds of formula I are those, wherein

X is —CH(OH)—, Y is —(CH$_2$)$_2$— and m is 1, or

X is —(CH$_2$)$_2$—, Y is —CH(OH)— and m is 1, or

X is —(CH$_2$)$_2$—, Y is —CH$_2$— and m is 1, or

X is —CH$_2$—. Y is —(CH$_2$)$_2$— and m is 2, or

X is —(CH$_2$)$_2$—, Y is —C(O)— and m is 1 and the other substituents are as described above.

Especially preferred are the following compounds:

4-[(RS)-hydroxy-[(2SR,5RS)-5-phenethyl-pyrrolidin-2-yl]-methyl]-phenol, 2-fluoro-4-[(RS)-hydroxy-[(2SR,5SR)-5-[2-(4-methoxy-phenyl)-ethyl]-pyrrolidin-2-yl]-methyl]-phenol, 4-[(RS)-hydroxy-[(2SR,5RS)-5-phenethyl-pyrrolidin-2-yl]-methyl]-benzene-1, 2-diol, 4-[(RS)-hydroxy-[(2SR,5SR)-5-[2-(4-methoxy-phenyl)-ethyl]-pyrrolidin-2-yl]-methyl]-phenol, 4-[hydroxy-[(2RS,6SR)-6-[2-(4-methoxy-phenyl)-ethyl]-piperidin-2-yl]-methyl]-phenol, (2RS,5RS)-4-[5-[2-(4-methoxy-phenyl)-ethyl]-pyrrolidin-2-ylmethyl]-phenol, (2RS,5RS)-4-(5-phenethyl-pyrrolidin-2-yl-methyl)-benzene-1,2-diol, (2RS,6SR)-4-[6-[2-(4-methoxy-phenyl)-ethyl]-piperidin2-ylmethyl]-phenol and Mixture of (2RS,5RS)- and (2RS,5SR)-(4-hydroxy-phenyl)-[5-[2-(4-methoxy-phenyl)-ethyl]-pyrrolidin-2-yl]-methanone.

Preferred compounds of formula II are those, wherein Y is —(CH$_2$)$_2$—, R$^1$, R$^2$ and R$^3$ are hydrogen, R$^4$ is hydroxy and m and p are 1.

Especially preferred are the following compounds:

(1RS,5SR,7aRS)-4-(5-phenethyl-tetrahydro-pyrrolo[1,2-c]oxazol-1-yl)-phenol and (1RS,5RS,7aSR)-4-(5-phenethyl-tetrahydro-pyrrolo[1,2-c]oxazol-1-yl)-phenol.

As mentioned earlier, compounds of formula I are known compounds. They can be prepared in accordance with the reactions of Scheme 1:

Scheme 1

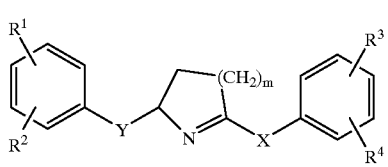

hydrogenation of a cyclic
imine (U.S. Pat. No. 4,569,941,
U.S. Pat. No. 4,548,951, EP 71399,
EP 71399, EP 50370)

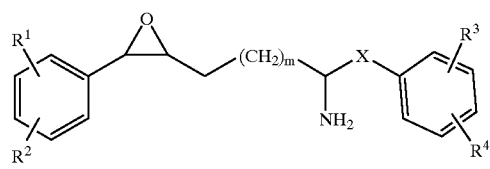

cyclisation of an amine epoxide, (U.S. Pat. No 4,543,361,
EP 115413, EP 71399)

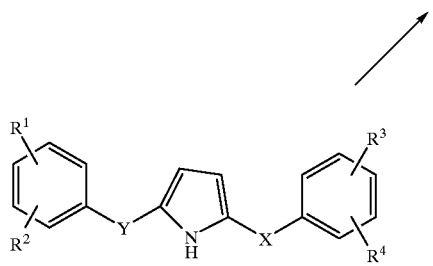

hydrogenation of a pyrrole
(EP 114758, U.S. Pat. No. 4,558,066,
EP 115413, U.S. Pat. No. 3,941,796,
J. Org. Chem., 49, 4203-4209, 1984)

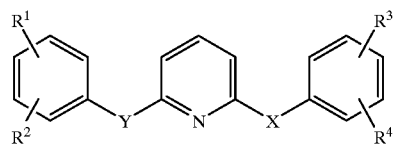

hydrogenation of a pyridine (EP 114758,
U.S. Pat. No. 4,558,066, EP 115413,
U.S. Pat. No 3,941,796)

alkylation of a compound of formula I
wherein $R^5$ is H

The novel compounds of formula II and their pharmaceutically acceptable salts can be prepared by methods known in the art, for example by processes described below, which comprises a) cyclizing a compound of formula I-1

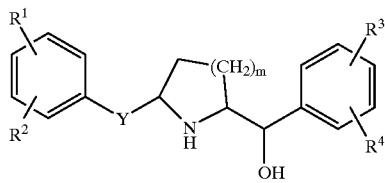

to a compound of formula II-1

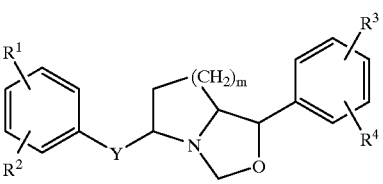

by reaction with a compound useful to form an oxazole ring, or, to a compound of formula II-2

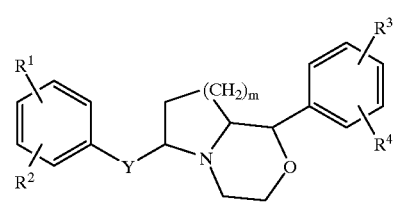

by reaction with a compound useful to form a morpholine ring, wherein $R^1$ and $R^2$ are, independently from each other, hydrogen, lower alkoxy, hydroxy, halogen, —$CONH_2$ or —C(O)O-lower alkyl; or taken together are —O—$CH_2$O;

$R^3$ and $R^4$ are, independently from each other, hydrogen, lower alkoxy, benzyloxy, halogen, hydroxy, —$CONH_2$ or —$SCH_3$; or taken together are —O—$CH_2$—O—;

Y is —CH(OH)—, —$(CH_2)_n$—, —C(O)— or —CH(lower alkoxy)—; and m is 1 or 2, or b) debenzylating a compound of formula II, wherein $R^3$ and/or $R^4$ are benzyloxy, or c) modifying one or more substituents $R^1$–$R^4$ within the definitions given above, and if desired, converting the compound obtained into a pharmaceutically acceptable acid addition salt.

Scheme 2 shows the processes for preparation of compounds of formula II from compounds of formula I.

Scheme 2

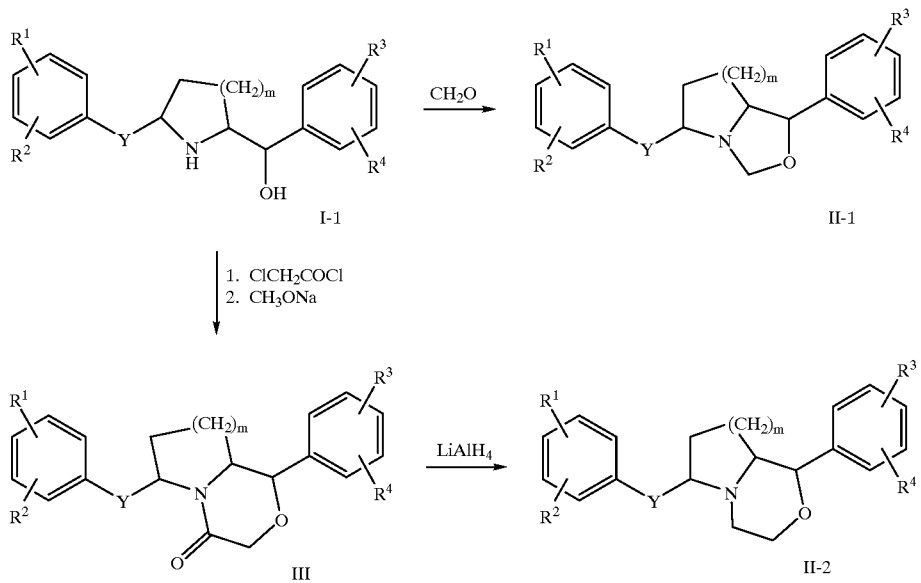

wherein
- $R^1$ and $R^2$ are, independently from each other, hydrogen, lower alkoxy, hydroxy, halogen, —$CONH_2$ or —C(O)O-lower alkyl; or taken together are —O—$CH_2$O—;
- $R^3$ and $R^4$ are, independently from each other, hydrogen, lower alkoxy, benzyloxy, halogen, hydroxy, —$CONH_2$ or —$SCH_3$; or taken together are —O—$CH_2$—O—;
- Y is —CH(OH)—, —$(CH_2)_n$—, —C(O)— or —CH(lower alkoxy)—; and
- m is 1 or 2.

Specific isomers may be manufactured in accordance with schemes 3 and 4.

Scheme 3

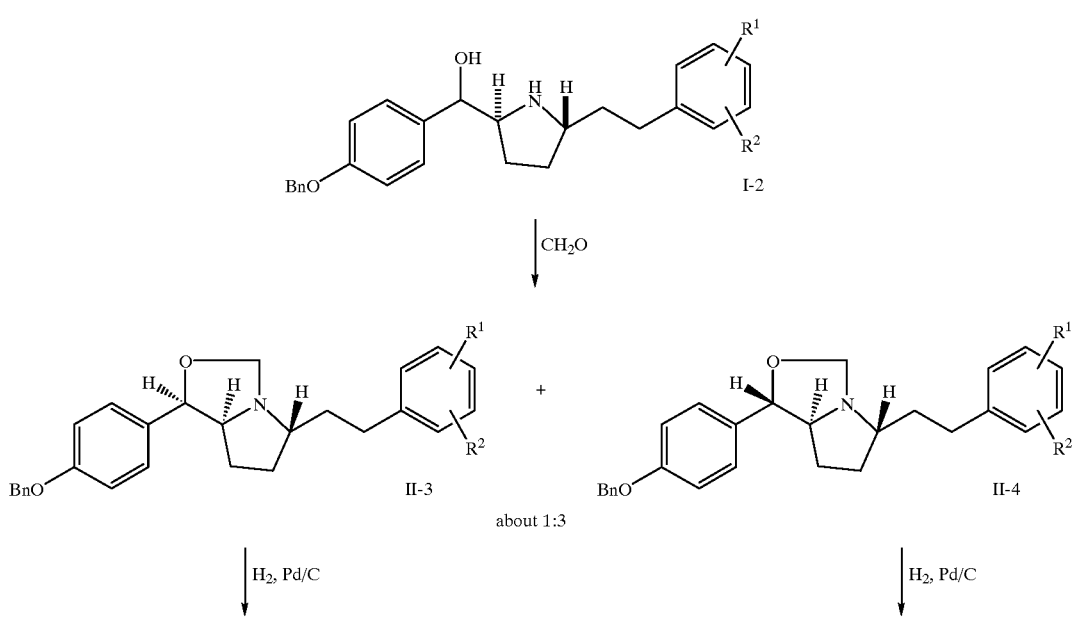

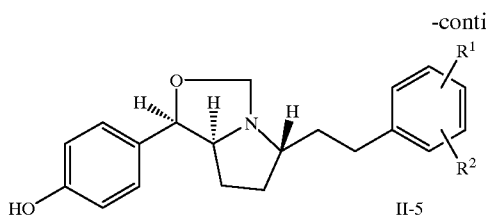

II-5

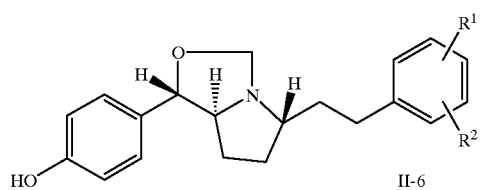

II-6 wherein
R[1] and R[2] are, independently from each other, hydrogen, lower alkoxy, hydroxy, halogen, —CONH$_2$ or —C(O)O-lower alkyl; or taken together are —O—CH$_2$O.

The detailed description of the above mentioned processes are described in Examples 35–42.

As mentioned earlier, the compounds of formula I and their pharmaceutically acceptable addition salts possess

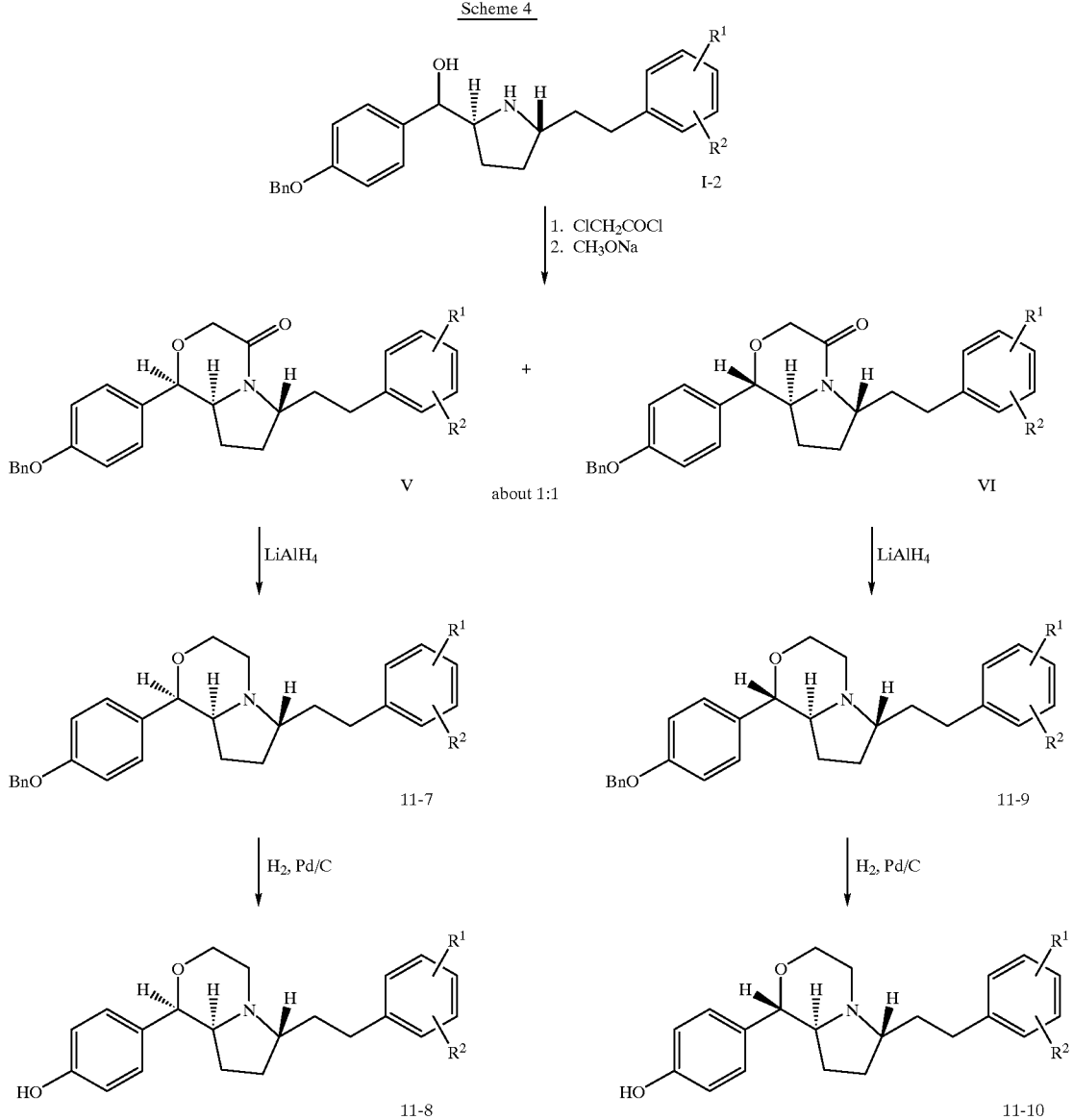

wherein
R[1] and R[2] are, independently from each other, hydrogen, lower alkoxy, hydroxy, halogen, —CONH$_2$ or —C(O)O-lower alkyl; or taken together are —O—CH$_2$O.

valuable pharmacodynamic properties which have been previously unrecognized. They are NMDA-receptor subtype selective blockers, which have a key function in modulating neuronal activity and plasticity which makes them key players in mediating processes underlying development of CNS as well as learning and memory formation.

The compounds were investigated in accordance with the test given hereinafter.

In the following test RO 25—6981 ([R-(R*,S*)]-a-(4-Hydroxy-phenyl)-b-methyl-4-(phenyl-methyl)-1-piperidine propanol) has been used as a high and selective blocker of N-methyl-D-aspartate (NMDA) receptor containing the NR2B subunit. The interaction of RO 25—6981 with NMDA receptors is characterized by the described test in vitro. The demonstration that RO 25-6981 is a highly selective, activity-dependent blocker of NMDA receptors is described in "Journ. of Pharmacology, Vol. 283, No.8, 1285–1297"

Method

3H-Ro 25-6981 binding (Ro 25-6981 is [R-(R*,S*)]-a-(4-Hydroxy-phenyl)-b-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 $\mu$g of protein/ml.

3H-Ro 25-6981 binding experiments were performed using a Tris-HCl 50 mM, pH 7.4 buffer. For displacement experiments 5 nM of 3H-Ro 25-6981 were used and non specific binding was measured using 10 $\mu$M of tetrahydroisoquinoline and usually it accounts for 10% of the total. The incubation time was 2 hours at 40° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide IC50 with their relative upper and lower 95% confidence limits (RS1, BBN, USA).

The thus-determined activity of the preferred compounds in accordance with the invention is in the range of 0.02–0.1 (in $\mu$M).

The following compounds of formula I have been tested and are preferred compounds for use according to the present invention:

| Ex. No. | $R^1$ | $R^2$ | $R^3$ | $R^4$ | $R^5$ | X | Y | m |
|---|---|---|---|---|---|---|---|---|
| 1 | H | H | 4-OH | H | H | —CH(OH)— | —(CH$_2$)$_2$— | 1 |
| 2 | 4-OCH$_3$ | H | 4-OH | 3-F | H | —CH(OH)— | —(CH$_2$)$_2$— | 1 |
| 3 | 4-OH | H | 4-OCH$_3$ | H | H | —(CH$_2$)$_2$— | —CH(OH)— | 2 |
| 4 | 4-OH | H | 4-OCH$_3$ | H | H | —(CH$_2$)$_2$— | —CH$_2$— | 1 |
| 5 | H | H | 4-OH | 3-OH | H | —CH(OH)— | —(CH$_2$)$_2$— | 1 |
| 6 | 4-OCH$_3$ | H | 4-OH | H | H | —CH$_2$— | —(CH$_2$)$_2$— | 2 |
| 7 | 4-OH | H | 4-OCH$_3$ | H | H | —(CH$_2$)$_2$— | —C(O)— | 1 |
| 8 | 4-OH | 3-OH | H | H | H | —(CH$_2$)$_2$— | —CH$_2$— | 1 |
| 9 | 4-OCH$_3$ | H | 4-OH | 3-OH | H | —CH$_2$— | —(CH$_2$)$_2$— | 1 |
| 10 | 4-OH | 3-OH | H | H | —(CH$_2$)$_2$CH$_3$ | —(CH$_2$)$_2$— | —CH$_2$— | 1 |
| 11 | 4-OH | 3-OH | H | H | —(CH$_2$)$_3$CH$_3$ | —(CH$_2$)$_2$— | —CH$_2$— | 1 |
| 12 | | together —OCH$_2$O— | | H | H | —CH(OH)— | —(CH$_2$)$_2$— | 1 |
| 13 | 4-OH | 3-CONH$_2$ | | together —OCH$_2$O— | H | —(CH$_2$)$_2$— | —CH(OH)— | 1 |
| 14 | H | H | H | H | H | —CH$_2$— | —(CH$_2$)$_2$— | 1 |
| 15 | H | H | H | H | H | —CH(OH)— | —(CH$_2$)$_2$— | 1 |
| 16 | 4-OCH$_3$ | H | 4-OH | 3-CONH$_2$ | H | —CH(OH)— | —(CH$_2$)$_2$— | 1 |
| 17 | 4-OH | 3-CONH$_2$ | 3-OCH$_3$ | H | H | —(CH$_2$)$_2$— | —CH(OH)— | 1 |
| 18 | 4-OH | H | 4-OH | 3-OH | H | —CH(OH)— | —(CH$_2$)$_2$— | 1 |
| 19 | 4-OCH$_3$ | H | H | H | H | —CH(OH)— | —(CH$_2$)$_2$— | 1 |
| 20 | 4-OH | H | 4-OH | 3-OH | H | —CH$_2$— | —(CH$_2$)$_2$— | 1 |
| 21 | 4-OCH$_3$ | H | 4-OH | 3-SCH$_3$ | H | —CH(OH)— | —(CH$_2$)$_2$— | 1 |
| 22 | H | H | 4-OH | H | H | —(CH$_2$)$_2$— | —CH(OH)— | 1 |
| 23 | 4-OH | 3-OH | 4-OH | H | (CH$_2$)$_2$CH$_3$ | —(CH$_2$)$_2$— | —CH$_2$— | 1 |
| 24 | 4-OH | 3-CONH$_2$ | 2-OCH$_3$ | 5—OCH$_3$ | H | —(CH$_2$)$_2$— | —CH(OH)— | 1 |
| 25 | | together —O—CH$_2$—O— | | together —O—CH$_2$—O— | H | —CH(OH)— | —(CH$_2$)$_2$— | 1 |
| 26 | | together —O—CH$_2$—O— | H | H | H | —(CH$_2$)$_2$— | —CH(OH)— | 1 |
| 27 | 4-OCH$_3$ | 3-OCH$_3$ | | together —O—CH$_2$—O— | H | —(CH$_2$)$_2$— | —CH(OH)— | 1 |
| 28 | 4-OCH$_3$ | H | | together —O—CH$_2$—O— | H | —(CH$_2$)$_2$— | —CH(OH)— | 1 |
| 29 | 4-OH | 3-CONH$_2$ | 2-OCH$_3$ | H | H | —(CH$_2$)$_2$— | —CH(OH)— | 1 |
| 30 | 4-OH | 3-CONH$_2$ | 2-OCH$_3$ | 3-OCH$_3$ | H | —(CH$_2$)$_2$— | —CH(OH)— | 1 |
| 31 | 4-OCH$_3$ | H | 4-OH | H | H | —CH(OH)— | —(CH$_2$)$_2$— | 1 |
| 32 | 4-OCH$_3$ | H | 4-OH | 3-OH | H | —CH(OH)— | —(CH$_2$)$_2$— | 1 |

-continued

| Ex. No. | R¹ | R² | R³ | R⁴ | R⁵ | X | Y | m |
|---|---|---|---|---|---|---|---|---|
| 33 | 4-OH | 3-COOCH₃ | together —O—CH₂—O— | | H | —(CH₂)₂— | —CH(OH)— | 1 |
| 34 | together —O—CH₂—O— | | 4-OCH₃ | 3-OCH₃ | H | —(CH₂)₂— | —CH(OH)— | 1 |

The preferred compounds are those of examples 1–26, 31 and 32, viz:

(1) 4-[(RS)-hydroxy-[(2SR,5RS)-5-phenethyl-pyrrolidin-2-yl]-methyl]-phenol,
(2) 2-fluoro-4-[(RS)-hydroxy-[(2SR,5SR)-5-[2-(4-methoxy-phenyl)-ethyl]-pyrrolidin-2-yl]-methyl]-phenol,
(3) 4-[hydroxy-[2RS,6SR)-6-[2-(4-methoxy-phenyl)-ethyl]-piperidin-2-yl]-methyl)-phenol,
(4) (2RS,5RS)-4-[5-[2-(4-methoxy-phenyl)-ethyl]-pyrrolidin-2-ylmethyl]-phenol,
(5) 4-[(RS)-hydroxy-[(2SR,5RS)-5-phenethyl-pyrrolidin-2-yl]-methyl]-benzene-1,2-diol,
(6) (2RS,6SR)-4-[6-[2-(4-methoxy-phenyl)-ethyl]-piperidin-2-ylmethyl]-phenol,
(7) Mixture of (2RS,5RS)- and (2RS,5SR)-(4-hydroxy-phenyl)-[5-[2-(4-methoxy-phenyl)-ethyl]-pyrrolidin-2-yl]-methanone,
(8) (2RS,5RS)-4-(5-phenethyl-pyrrolidin-2-yl-methyl)-benzene-1,2-diol,
(9) (2RS,5RS)-4-[5-[2-(4-methoxy-phenyl)-ethyl]-pyrrolidin-2-ylmethyl]-benzene-1,2-diol,
(10) (2RS,5RS)-4-(1-butyl-5-phenethyl-pyrrolidin-2-ylmethyl)-benzene-1,2-diol,
(11) (2RS,5RS)-4-(5-phenethyl-1-propyl-pyrrolidin-2-ylmethyl)-benzene-1,2-diol,
(12) (RS)-[(2SR,5SR)-5-(2-benzo[1.3]dioxol-5-yl-ethyl)-pyrrolidin-2-yl]-phenyl-methanol,
(13) 5-[(RS)-[(2SR,5SR)-5-(2-benzo[1.3]dioxol-5-yl-ethyl)-pyrrolidin-2]-hydroxy-methyl]-2-hydroxy-benzamide,
(14) (2RS,5RS)-2-benzyl-5-phenethyl-pyrrolidine,
(15) (RS)-[(2SR,5SR)-5-phenethyl-pyrrolidin-2-yl]-phenyl-methanol,
(16) 2-hydroxy-5-[(RS)-hydroxy-[(2SR,5SR)-5-[2-(4-methoxy-phenyl)-ethyl]-pyrrolidin-2-yl]-methyl]-benzamide,
(18) 4-[(RS)-hydroxy-[(2SR,5RS)-5-[2-(4-hydroxy-phenyl)-ethyl]-pyrrolidin-2-yl]-methyl]-benzene-1,2-diol,
(19) (RS)-[(2SR,5SR)-5-[2-(4-methoxy-phenyl)-ethyl]-pyrrolidin-2-yl]-phenyl-methanol,
(20) 4-[2RS,5SR)-5-[2-(4-hydroxy-phenyl)-ethyl]-pyrrolidin-2-ylmethyl]-benzene-1,2-diol,
(21) 4-[(RS)-hydroxy-[(2SR,5SR)-5-[2-(4-methoxy-phenyl)-ethyl]-pyrrolidin-2-yl]-methyl]-2-methylsulfanyl-phenol,
(22) 4-[2-[(2RS,5RS)-5-[(SR)-hydroxy-phenyl-methyl]-pyrrolidin-2-yl]-ethyl]-phenol,
(23) (2RS,5RS)-4-[5-[2-(4-hydroxy-phenyl)-ethyl]-1-propyl-pyrrolidin-2-ylmethyl]-benzene-1,2-diol,
(24) 5-[(RS)-[(2SR,5SR)-5-[2-(2, 5-dimethoxy-phenyl)-ethyl]-pyrrolidin-2-yl]-hydroxy-methyl]-2-hydroxy-benzamide,
(25) (RS)-benzo[1.3]dioxol-5-yl-[(2SR,5SR)-5-yl-ethyl)-pyrrolidin-2-yl]-menthanol,
(26) (RS)-benzo[1.3]dioxol-5-yl-[(2SR,5SR)-5-phenethyl-pyrrolidin-2-yl]-methanol,
(31) 4-[(RS)-hydroxy-[(2SR,5SR)-5-[2-(4-methoxy-phenyl)-ethyl]-pyrrolidin-2-yl]-methyl]-benzene-1,2-diol,
(32) 4-[(RS)-hydroxy-[(2SR,5SR)-5-[2-(4-methoxy-phenyl)-ethyl]-pyrrolidin-2-yl]-methyl]-phenol.

The following compounds of formula II have been tested:

| Ex. No. | R¹ | R² | R³ | R⁴ | Y | m | p |
|---|---|---|---|---|---|---|---|
| 35 | H | H | 4-OH | H | —(CH₂)₂— | 1 | 2 |
| 36 | H | H | 4-OH | H | —(CH₂)₂— | 1 | 2 |
| 37 | H | H | 4-OH | H | —(CH₂)₂— | 1 | 1 |
| 38 | H | H | 4-OH | H | —(CH₂)₂— | 1 | 1 |

Compounds of Examples 35–38 are:

(35) (1RS,6SR,8aRS)-4-(6-phenethyl-hexahydro-pyrrolo[2,1-c][1, 4]oxazin-1-yl)-phenol,
(36) (1RS,6RS,8aSR)-4-(6-phenethyl-hexahydro-pyrrolo[2,1-c][1, 4]oxazin-1-yl)-phenol,
(37) (1RS,5RS,7aSR)-4-(5-phenethyl-tetrahydro-pyrrolo[1,2-c]oxazol-1-yl)-phenol and
(38) (1RS,5SR,7aRS)-4-(5-phenethyl-tetrahydro-pyrrolo[1,2-c]oxazol-1-yl)-phenol Please find below some $IC_{50}$-values of compounds, described above:

| Example-No. | $IC_{50}$(μmol) |
|---|---|
| 1 | 0,02 |
| 2 | 0,03 |
| 3 | 0,03 |
| 4 | 0,04 |
| 5 | 0.04 |
| 6 | 0,045 |
| 7 | 0,07 |
| 35 | 0,09 |
| 37 | 0,05 |

The compounds of formula I and II and their salts, as herein described, together with pharmaceutically inert excipients can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. Examples of pharmaceutical preparations in solid form are tablets, suppositories, capsules, or in liquid form are solutions, suspensions or emulsions. Pharmaceutical adjuvant materials include preservatives, stabilizers, wetting or emulsifying agents, salts to change the osmotic pressure or to act as buffers. The pharmaceutical preparations can also contain other therapeutically active substances.

The daily dose of compounds of formula I and II to be administered varies with the particular compound employed, the chosen route of administration and the recipient. Representative of a method for adninistering the compounds of formula I and II is by the oral and parenteral type administration route. An oral formulation of a compound of formula I and II is preferably administered to an adult at a dose in the range of 1 mg to 1000 mg per day. A parenteral formulation of a compound of formula I is preferably administered to an adult at a dose in the range of from 5 to 500 mg per day.

The invention is further illustrated in the following examples.

EXAMPLE 35

(1RS ,6SR,8aRS)-4-(6-Phenethyl-hexahydro-pyrrolo [2,1-c][1,4]oxazin-1-yl)-phenol (1RS,6SR,8aRS)-1-(4-Benzyloxy-phenyl)-6-phenethyl-hexahydro-pyrrolo[2, 1-c][1,4]oxazine (0.09 g, 0.22 mmol) was dissolved in MeOH (5 ml) and hydrogenated in the presence of Pd on C at room temperature and at atmospheric pressure for 4 hours. After filtration and evaporation of the solvent the residue was chromatographed over silica gel ($CH_2Cl_2$—MeOH 19:1) to provide (1RS,6SR,8aRS)-4-(6-phenethyl-hexahydro-pyrrolo[2,1-c][1, 4]oxazin-1-yl)-phenol (25 mg, 35%) as a pink solid, m.p. 170–172° C. MS: m/e=324.3 (M+H$^+$).

Following the general method of example 35 the compounds of examples 36 to example 38 were prepared.

EXAMPLE 36

(1RS,6RS,8aSR)-4-(6-Phenethyl-hexahydro-pyrrolo[2,1-c][1,4]oxazin-1-yl)-phenol

The title compound, MS: m/e=324.3 (M+H$^+$), was prepared from (1RS,6RS,8aSR)-1-(4-benzyloxy-phenyl)-6-phenethyl-hexahydro-pyrrolo[2,1-c][1,4]oxazine.

EXAMPLE 37

(1RS, 5RS,7aSR)-4-(5-Phenethyl-tetrahydro-pyrrolo[1,2-c] oxazol-1yl)-phenol

The title compound, MS: m/e=310.3 (M+H$^+$), was prepared from (1RS,5RS,7aSR)-1-(4-benzyloxy-phenyl)-5-phenethyl-tetrahydro-pyrrolo[1,2-c]oxazole.

EXAMPLE 38

(1RS,5SR,7aRS)-4-(5-Phenethyl-tetrahydro-pyrrolo[1,2-c] oxazol-l-yl)-phenol

The title compound, m.p. 176 ° C. and MS: m/e=310.2 (M+H$^+$), was prepared from (1RS,5SR,7aRS)-1-(4-benzyloxy-phenyl)-5-phenethyl-tetrahydro-pyrrolo[1,2-c] oxazole.

EXAMPLE 39

(1RS,5RS,7aSR)-1-(4-Benzyloxy-phenyl)-5-phenethyl-tetrahydro-pyrrolo[1,2-c]oxazole and (1RS,5SR,7aRS)-1-(4-Benzyloxy-phenyl)-5-phenethyl-tetrahydro-pyrrolo[1,2-c]oxazole A mixture of (RS)- and (SR)-[(2RS,5SR)-4-benzyloxy-phenyl)-5-phenethyl-pyrrolidin-2-yl]-methanol (0.24 g, 0.62 mmol) was stirred in the presence of an aqueous solution of formaldehyde (36% in $H_2O$, 2 ml) for 2 hours at room temperature. Reaction mixture was then diluted with $H_2O$ (10 ml), basified to pH 13 with 1N NaOH and extracted with ether (3x 20 ml). Combined organic phases were dried over $Na_2SO_4$, and concentrated. The residue was chromatographed over silica gel (hexane-ethyl acetate 1:1) to provide (1RS,5RS,7aSR)-1-(4-benzyloxy-phenyl)-5-phenethyl-tetrahydro-pyrrolo[1,2-c]oxazole (0.065 g, 26%) as a yellowish solid, m.p. 101–103° C. MS: m/e=400.3 (M+H$^+$) and (1RS,5SR,7aRS)-1-(4-benzyloxy-phenyl)-5-phenethyl-tetrahydro-pyrrolo[1,2-c]oxazole as a white solid, m.p. 94–95° C. MS: m/e=400.3 (M+H$^+$).

EXAMPLE 40

(1RS,6RS,8aSR)-1-(4-Benzyloxy-phenyl)-6-phenethyl-hexahydro-pyrrolo[2,1-c][1,4]oxazine A solution of (1RS,6RS,8aSR)-1-(4-Benzyloxy-phenyl)-6-phenethyl-tetrahydro-pyrrolo[2, 1-c][1,4]oxazin-4-one (0.12 g, 0.28 mmol) in THF (1 ml) was added dropwise to a 0° C. suspension of LiAlH$_4$ ( 0.021 g, 0.56 mmol) in THF (1 ml). Reaction mixture was stirred at room temperature for 2 hours then cooled to 0° C. and treated successively with $H_2O$ (25 ml), 5N NaOH (25 ml), $H_2O$ (75 ml). Reaction mixture was stirred at room temperature for 30 min. and $Na_2SO_4$ was added. After filtration, evaporation of the solvent provided (1RS,6RS,8aSR)-1-(4-benzyloxy-phenyl)-6-phenethyl-hexahydro-pyrrolo[2,1-c][1,4]oxazine (90 mg, 78%) as a colorless oil. MS: m/e=414.5 (M+H$^+$). Following the general method of example 40 the compound of example 41 was prepared.

EXAMPLE 41

(1RS,6SR,8aRS)-1-(4-Benzyloxy-phenyl)-6-phenethyl-hexahydro-pyrrolo[2, 1-c][1,4]oxazine The title compound, MS: m/e=414.2 (M+H$^+$), was prepared from (1RS,6SR,8aRS)-1-(4-benzyloxy-phenyl)-6-phenethyl-tetrahydro-pyrrolo[2, 1-c][1,4]oxazin-4-one.

EXAMPLE 42

(1RS,6RS,8aSR)-1-(4-Benzyloaxy-phenyl)-6-phenethyl-tetrahydro-pyrrolo[2,1-c][1,4 ]oxazin-4-one and (1RS,6SR, 8aRS)-1-(4-Benzyloxy-phenyl)-6-phenethyl-tetrahydro-pyrrolo[2,1-c][1,4]oxazin-4-one A mixture of (RS)- and (SR)-[(2RS,5SR)-4-Benzyloxy-phenyl)-5-phenethyl-pyrrolidin-2-yl]-methanol (0.38 g, 1 mmol), and triethylamine (0.42 ml, 3 mmol) in dioxan (10 ml) was treated at 5° C. with chloroacetylchloride (96 ml, 1.2 mmol). After 1.2 hour stirring at room temperature, reaction mixture was quenched with $H_2O$ (10 ml), acidified to pH 2 with 1N HCl and extracted with $CH_2Cl_2$ (3×30 ml). Combined organic phases were washed with saturated NaCl (20 ml), dried over $Na_2SO_4$, and concentrated. Residue was dissolved in toluene (8 ml) and refluxed in the presence of sodium methylate (0.13 g, 2.4 mmol) for 4 hours. Reaction mixture was cooled to room temperature and solvent was evaporated. Residue was diluted with $H_2O$ (10 ml), acidified to pH 2 with 1N HCl and extracted with $CH_2Cl_2$ (3×30 ml). Combined organic phases were washed with $H_2O$ (20 ml), dried over $Na_2SO_4$, and concentrated. The residue was chromatographed over silica gel (hexane-ethyl acetate 4:1 then 1:1) to provide (1RS,6RS,8aSR)-1-(4-benzyloxy-phenyl)-6-phenethyl-tetrahydro-pyrrolo[2,1-c][1,4]oxazin-4-one (0.125 g, 30%) as a yellow oil, MS: m/e=428.4 (M+H$^+$) and (1RS,6SR,8aRS)-1-(4benzyloxy-phenyl)-6-phenethyl-tetrahydro-pyrrolo[2,1-c][1,4]oxazin-4-one (0.127 g, 30%) as a yellow oil. MS: m/e=428.3 (M+H$^+$).

(RS)- and (SR)-[(2RS,5SR)-4-Benzyloxy-phenyl)-5-phenethyl-pyrrolidin-2-yl]-methanol can be prepared by hydrogenation of a pyrrole as described in J. Org. Chem. 1984, 49, 4203–4209.

EXAMPLE A

Tablet Formulation (Wet Granulation)

| Ingredients | mg/tablet | | | |
|---|---|---|---|---|
| 1. Active compound | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| TOTAL | 167 | 167 | 167 | 831 |

Manufacturing Procedure:

1. Mix Items 1, 2, 3 and 4 and granulate with purified water
2. Dry the granulation at 50° C.
3. Pass the granulation through suitable milling equipment.
4. Add Item 5 and mix for three minutes; compress on a suitable press.

Capsule Formulation

| Ingredients | mg/capsule | | | |
|---|---|---|---|---|
| 1. Active compound | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| TOTAL | 200 | 200 | 300 | 600 |

Manufacturing Procedure:

1. Mix Items 1, 2, and 3 in a suitable mixer for 30 minutes.
2. Add Items 4 and 5 and mix for 3 minutes.
3. Fill into a suitable capsule.

Tablet Formulation (Wet Granulation)

| Ingredients | mg/tablet | | | |
|---|---|---|---|---|
| 1. Active compound | 5 | 25 | 100 | 500 |
| 2. Lactose Anhydrous | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 2 | 2 | 5 |
| TOTAL | 167 | 167 | 167 | 835 |

Manufacturing Procedure:

1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

We claim:

1. A method of treating a disease in a mammal caused by over activation of NMDA receptor subtypes comprising administering to said mammal in need thereof a compound of formula II

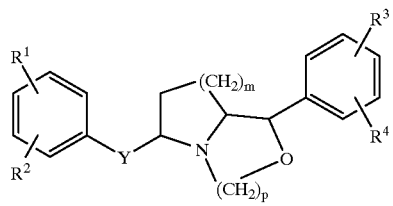

wherein $R^1$ and $R^2$ are, independently from each other, hydrogen, lower alkoxy, hydroxy, halogen, —$CONH_2$ or —C(O)O-lower alkyl; or taken together are —O—$CH_2$O—;

$R^3$ and $R^4$ are, independently from each other, hydrogen, lower alkoxy, benzyloxy, halogen, hydroxy, —$CONH_2$ or —$SCH_3$; or taken together are —O—$CH_2$—O—;

Y is —CH(OH)—, —$(CH_2)_n$—, —C(O)— or —CH(lower alkoxy)—; and m, n and p are 1 or 2;

or a pharmaceutically acceptable salt thereof and a therapeutically acceptable carrier in an amount which is effective in treating disease caused by over activation of NMDA receptor subtypes.

2. The method according to claim 1, wherein the compound of formula II, Y is —$(CH_2)_2$—, $R^1$, $R^2$ and $R^3$ are hydrogen, $R^4$ is hydroxy and m and p are 1.

3. The method according to claim 1, wherein the compound is selected from the group consisting of (1RS,5SR,7aRS)-4-(5-phenethyl-tetrahydro-pyrrolo[1,2-c]oxazol-1-yl)-phenol and (1RS,5RS,7aSR)-4-(5-phenethyl-tetrahydro-pyrrolo[1,2-c]oxazol-1-yl)-phenol.

4. A compound of formula

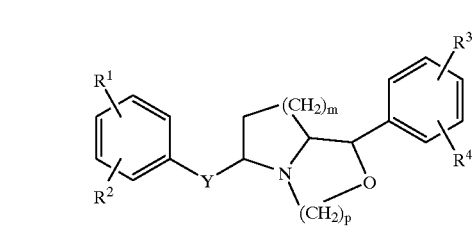

wherein $R^1$ and $R^2$ are, independently from each other, hydrogen, lower alkoxy, hydroxy, halogen, —$CONH_2$ or —C(O)O-lower alkyl; or taken together are —O—$CH_2$O—;

$R^3$ and $R^4$ are, independently from each other, hydrogen, lower alkoxy, benzyloxy, halogen, hydroxy, —$CONH_2$ or —$SCH_3$; or taken together are —O—$CH_2$—O—;

Y is —CH(OH)—, —$(CH_2)_n$—, —C(O)— or —CH(lower alkoxy)—; and m, n and p are 1 or 2;

a pharmaceutically acceptable addition salt thereof.

5. A pharmaceutical composition comprising a therapeutically effective amount of a compound of the formula

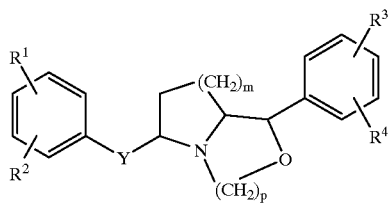

II wherein
R$^1$ and R$^2$ are, independently from each other, hydrogen, lower alkoxy, hydroxy, halogen, —CONH$_2$ or —C(O)O-lower alkyl; or taken together are —O—CH$_2$O;

R$^3$ and R$^4$ are, independently from each other, hydrogen, lower alkoxy, benzyloxy, halogen, hydroxy, —CONH$_2$ or —SCH$_3$; or taken together are —O—CH$_2$—O—;

Y is —CH(OH)—, —(CH$_2$)$_n$—, —C(O)— or —CH(lower alkoxy)—; and m, n and p are 1 or 2;

or a pharmaceutically acceptable addition salt thereof and a pharmaceutically acceptable carrier.

* * * * *

UNITED STATES PATENT AND TRADEMARK OFFICE
CERTIFICATE OF CORRECTION

PATENT NO. : 6,015,824
DATED : January 18, 2000
INVENTOR(S) : Alanine et al.

It is certified that error appears in the above-identified patent and that said Letters Patent is hereby corrected as shown below:

In claim 1, column 17, line 64, after "mammal" and before "caused" insert -- in need thereof --

In claim 4, column 18, line 67, delete "a pharmaceutically acceptable addition salt thereof." and insert therefor -- or a pharmaceutically acceptable salt thereof. --

In claim 5, column 20, line 12, delete "addition".

Signed and Sealed this

Third Day of April, 2001

Attest:

NICHOLAS P. GODICI

Attesting Officer

Acting Director of the United States Patent and Trademark Office